United States Patent
Kothrade et al.

(10) Patent No.: US 6,284,803 B1
(45) Date of Patent: Sep. 4, 2001

(54) SOLID DOSAGE FORM WITH POLYMERIC BINDER

(75) Inventors: Stephan Kothrade, Limburgerhof; Gunther Berndl, Herxheim; Helmut Meffert, Mannheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/395,775

(22) Filed: Sep. 14, 1999

(30) Foreign Application Priority Data

Sep. 24, 1998 (DE) .............................. 198 43 904

(51) Int. Cl.[7] .............................. A61K 47/30; A61K 9/20; A61K 9/32; A61K 9/42
(52) U.S. Cl. .................................. 514/772.1; 514/772.2; 424/465; 424/476; 424/482
(58) Field of Search .............................. 514/772.1, 772.2; 424/465, 476, 482

(56) References Cited

U.S. PATENT DOCUMENTS

| | | |
|---|---|---|
| 3,900,559 | 8/1975 | Sim ........................................ 424/22 |
| 4,224,427 | 9/1980 | Mueller et al. ........................ 526/93 |
| 4,248,855 | 2/1981 | Blank et al. ............................ 424/19 |
| 4,749,576 | 6/1988 | Lee ........................................ 424/486 |
| 4,801,460 | 1/1989 | Goertz et al. ........................ 424/465 |
| 4,880,585 | 11/1989 | Klimesch et al. .................... 264/141 |
| 4,957,681 | 9/1990 | Klimesch et al. .................... 264/211 |
| 5,073,379 | 12/1991 | Klimesch et al. .................... 424/467 |
| 5,202,128 | 4/1993 | Morella et al. ....................... 424/469 |
| 5,330,766 | 7/1994 | Morella et al. ....................... 424/490 |
| 5,378,474 | 1/1995 | Morella et al. ....................... 424/469 |
| 5,567,768 | * 10/1996 | Amici et al. ........................... 525/57 |

FOREIGN PATENT DOCUMENTS

WO 89/06957   8/1989   (WO) .

* cited by examiner

Primary Examiner—Russell Travers
Assistant Examiner—S. Wang
(74) Attorney, Agent, or Firm—Keil & Weinkauf

(57) ABSTRACT

The present invention relates to a solid dosage form comprising at least one polymeric binder and at least one active ingredient and, where appropriate, conventional additives, wherein the polymeric binder consists of copolymerized units a) 15–83% by weight of at least one N-vinyllactam, b) 15–83% by weight of methyl methacrylate, c) 2–70% by weight of at least one other monomer and d) 0–9.9% by weight of at least one $\alpha,\beta$-ethylenically unsaturated acid.

4 Claims, No Drawings

SOLID DOSAGE FORM WITH POLYMERIC BINDER

The invention relates to solid dosage forms comprising at least one polymeric binder and at least one active ingredient and, where appropriate, conventional additives and to a process for producing the solid dosage form.

Solid dosage forms comprising physiologically tolerated polymers as binders are becoming increasingly important, especially for dosage forms with delayed release of active ingredient. Thus, EP-A 609 961 describes solid dosage forms based on physiologically tolerated copolymers, which have a core/shell structure of various copolymers in order to achieve uniform release of active ingredient.

WO 89/06957 describes pharmaceutical formulations with controlled release of active ingredient in which the N-vinylpyrrolidone/alkyl (meth)acrylate copolymer employed as binder makes it possible, because of its large swelling capacity of from 50% to 250%, to delay release of active ingredient.

U.S. Pat. No. 3,900,559 describes active ingredient compositions with delayed release of active ingredient based on crosslinked copolymers, which comprise, inter alia, N-vinyllactams and (meth)acrylates, in particular (meth) acrylates of di- and polyols, as comonomers. In this case, the active ingredient is preferably introduced by impregnating the polymer with a solution of the active ingredient or by polymerizing the monomers in the presence of the dissolved active ingredient.

In order to achieve delayed release of active ingredient, in U.S. Pat. No. 4,248,855 the polymers which are employed as binders and contain acid groups are dissolved, a solution of a salt-forming active ingredient is added, and the active ingredient/polymer salt is formulated for pharmaceutical use. In order to achieve adequate solubility, the binder contains at least 75% by weight of hydrophilic monomers; in turn, at least 10% by weight of these are monomers containing acid groups in order to make it possible to bind the active ingredient in the form of its salt.

The prior art solid dosage forms mentioned have the disadvantage that the introduction of the active ingredient and/or its release take place by diffusion. Moreover, the release is coupled to the great swelling capacity of the binder, and thus depends on the diffusion characteristics of the particular active ingredient in the particular binder. The introduction of the active ingredient and/or the production of the solid dosage form requires elaborate or multistage processes in order to achieve the desired delayed release. In addition, the conventional processes for producing solid pharmaceutical dosage forms, especially tablets, are carried out batchwise and comprise a plurality of stages.

A considerably simpler continuous process for producing solid pharmaceutical dosage forms, in which an active ingredient-containing, solvent-free melt of a polymeric binder is extruded, and the extrudate is shaped to the required dosage form, for example in a calender with molding rolls, is disclosed in EP-A 240 904, EP-A 240 906, EP-A 337 256 and EP-A 358 105 (melt extrusion).

EP-A 240 904 mentions as polymeric binders polyvinylpyrrolidone or copolymers of N-vinylpyrrolidone with, inter alia, vinyl esters, unsaturated carboxylic acids, including acrylic acid and methacrylic acid, their amides and their esters with $C_1$–$C_{12}$-alkanols. In the examples, vinylpyrrolidone/vinyl acetate copolymers are employed. The N-vinylpyrrolidone/vinyl acetate copolymers have, just like the N-vinylcaprolactam polymers and copolymers disclosed in DE 197 53 300.0, a very favorable profile of properties as binders for producing solid dosage forms by compression at elevated temperature and, in particular, by melt extrusion, but they have the disadvantage that they release the active ingredient relatively rapidly.

It is an object of the present invention to provide solid dosage forms which make slow release of the active ingredient possible and can be produced straightforwardly and cost-effectively, e.g. by melt extrusion.

We have found that this object is achieved by using as binder a polymer of at least one N-vinyllactam, methyl methacrylate, at least one other copolymerizable monomer and, where appropriate, up to 9.9% by weight of at least one copolymerizable carboxylic acid.

The present invention therefore relates to a solid dosage form comprising at least one polymeric binder and at least one active ingredient and, where appropriate, conventional additives, wherein the polymeric binder comprises as copolymerized units a) 15–83% by weight of at least one N-vinyllactam of the formula I

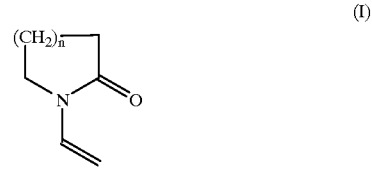

in which n is 1, 2 or 3, b) 15–83% by weight of methyl methacrylate, c) 2–70% by weight of at least one other monomer selected from vinyl esters of aliphatic $C_1$–$C_{22}$-carboxylic acids, esters of $\alpha,\beta$-ethylenically unsaturated $C_3$–$C_8$-mono- and dicarboxylic acids with $C_1$–$C_8$-alkanols, $C_1$–$C_4$-diols or di-($C_1$–$C_4$)-alkylamino-$C_1$–$C_4$-alkanols, amides, nitriles and cyclic anhydrides of these carboxylic acids, and d) 0–9.9% by weight of at least one $\alpha,\beta$-ethylenically unsaturated acid selected from $C_3$–$C_8$-mono- and -dicarboxylic acids, noncyclic anhydrides of these carboxylic acids, monoesters of the $C_3$–$C_8$-dicarboxylic acids, $\alpha,\beta$-ethylenically unsaturated sulfonic acids and the salts or quaternized products thereof, where the amounts of the monomers add up to 100% by weight.

The polymer used as binder comprises preferably 25–75% by weight and particularly preferably 30–65% by weight of at least one N-vinyllactam of the formula I as copolymerized units. The binder may comprise a mixture of N-vinyllactams of the formula I, but the binder preferably comprises one N-vinyllactam, as copolymerized units. Preferred N-vinyllactams of the formula I are N-vinylpyrrolidone, N-vinylpiperidone and N-vinylcaprolactam; N-vinylpyrrolidone is particularly preferred. The binder comprises preferably 20–70% by weight and particularly preferably 20–55% by weight of methyl methacrylate as comonomer.

In addition, the polymeric binder comprises at least one other copolymerizable monomer (further monomer c)) in an amount of 2–70% by weight, preferably 5–55% by weight and particularly preferably 15–50% by weight, based on the total weight of the monomers. Particularly suitable as further monomer c) are vinyl esters of aliphatic $C_1$–$C_{22}$-carboxylic acids, such as vinyl formate, vinyl acetate, vinyl propionate, vinyl butyrate, vinyl valerate, vinyl caproate, vinyl octanoate, vinyl caprate, vinyl laurate, vinyl myristate and vinyl palmitate, with vinyl acetate being particularly preferred. Also suitable as further monomer c) are, for example, the esters of monoethylenically unsaturated carboxylic acids having 3 to 8 carbon atoms, such as acrylic acid, methacrylic acid, dimethacrylic acid, ethacrylic acid, maleic acid, citraconic acid, methylenemalonic acid, allylacetic acid, vinylacetic acid, crotonic acid, fumaric acid, mesaconic acid and itaconic acid, with $C_1$–$C_8$-alkanols, apart from methyl methacrylate, with $C_1$–$C_4$-diols, with mono- and di-$C_1$–$C_4$-alkylamino-$C_1$–$C_4$-alkanols, and the amides, mono- and di-$C_1$–$C_4$-alkylamides and nitriles of these carboxylic acids, e.g. methyl acrylate, ethyl acrylate, propyl acrylate, n-butyl acrylate, 2-ethylhexyl acrylate, ethyl methacrylate, propyl methacrylate, n-butyl methacrylate, 2-ethylhexyl methacrylate, hydroxyethyl acrylate, hydroxypropyl acrylate, hydroxybutyl acrylate, hydroxyisobutyl acrylate, hydroxyethyl methacrylate, hydroxypropyl methacrylate, hydroxybutyl methacrylate, hydroxyisobutyl methacrylate, dimethyl maleate, diethyl maleate, dibutyl maleate, acrylamide, methacrylamide, N,N-dimethylacrylamide, N-tert-butylacrylamide, acrylonitrile, methacrylonitrile, dimethylaminoethyl acrylate, diethylaminoethyl acrylate, diethylaminoethyl methacrylate and the salts of the last-mentioned monomers with carboxylic acids or mineral acids or the quaternized products. It is, of course, also possible to employ mixtures of said monomers.

In addition, the polymeric binder may also comprise 0–9.9% by weight, in particular 0–7% by weight, preferably 0–5% by weight, of at least one α,β-ethylenically unsaturated acid, in particular monoethylenically unsaturated carboxylic acid having 3 to 8 carbon atoms, such as acrylic acid, methacrylic acid, dimethacrylic acid, ethacrylic acid, maleic acid, citric acid, methylenemalonic acid, allylacetic acid, vinylacetic acid, crotonic acid, fumaric acid, mesaconic acid and itaconic acid, and the monoesters of said dicarboxylic acids with $C_1$–$C_8$-alkanols, e.g. monomethyl maleate, monoethyl maleate, monobutyl maleate. Acrylic acid, methacrylic acid, maleic acid or mixtures of said carboxylic acids are preferred. The monoethylenically unsaturated carboxylic acids can be employed in the form of the free acid, the anhydrides or in partially or completely neutralized form. The neutralization is preferably carried out using alkali metal or alkaline earth metal bases, ammonia or amines, e.g. sodium hydroxide, potassium hydroxide, sodium carbonate, potassium carbonate, sodium bicarbonate, magnesium oxide, calcium hydroxide, calcium oxide, gaseous or aqueous ammonia, triethylamine, ethanolamine, diethanolamine, morpholine, diethylenetriamine or tetraethylenepentamine. Also suitable as copolymerizable α,β-ethylenically unsaturated acid is acrylamidoglycolic acid, vinylsulfonic acid, allylsulfonic acid, methallylsulfonic acid, styrenesulfonic acid, 3-sulfopropyl acrylate, 3-sulfopropyl methacrylate and acrylamidomethylpropanesulfonic acid, and phosphono-containing monomers such as vinylphosphonic acid, allylphosphonic acid and acrylamidomethylpropanephosphonic acid. It is, of course, also possible to employ mixtures of said monomers. If present, in general at least 0.1% by weight, preferably at least 0.5% by weight, of at least one monomer containing acid groups is copolymerized.

In preferred embodiments of the present invention, the polymeric binders contain no monomer containing acid groups in the copolymer.

In addition, the polymeric binder may, where appropriate, also comprise 0.1–10% by weight of at least one other copolymerizable monomer e), e.g. N-vinylimidazole, N-vinyl-2-methylimidazole, N-vinyl-4-methylimidazole, and vinylaromatic compounds such as styrene.

The polymeric binder may, where appropriate, additionally comprise 0.1–2.0% by weight of at least one crosslinking monomer. Crosslinking monomers mean in this connection essentially di-, tri- and polyolefinic monomers and macromers. Suitable crosslinking monomers comprise, for example, the di-, tri- or polyesters of ethylenically unsaturated carboxylic acids with low molecular weight, dihydric, trihydric or polyhydric alcohols, preferably the acrylic and methacrylic esters of dihydric, trihydric and polyhydric alcohols, such as ethylene glycol, propylene glycol and the more highly condensed representatives thereof, e.g. diethylene glycol, triethylene glycol, dipropylene glycol and tripropylene glycol, and butanediol, pentanediol, hexanediol, propanetriol and trimethylolpropane. Likewise suitable are polyether (meth)acrylates, polyester (meth)acrylates and polyurethane (meth)acrylates having two or more α,β-ethylenically unsaturated groups. Likewise suitable are the di-, tri- and polyethers of said di- and polyfunctional alcohols with vinyl alcohol, and vinylaromatic compounds such as di- and trivinylbenzene, divinylureas, e.g. divinylmethyleneurea, and diallylamines such as diallylamine and diallylammonium chloride. Further crosslinking monomers and macromers are known to the skilled worker and described, for example, in P. K. T. Oldring (editor), Chemistry and Technology of UV- and EB-Formulations for Coatings and Paints, Vol. II, SITA Technology, London 1991.

In particularly preferred embodiments of the present invention, the polymeric binders essentially comprise 30–65% by weight of N-vinylpyrrolidone, 20–60% by weight of methyl methacrylate and 15–50% by weight of vinyl acetate as copolymerized units.

As a rule, the water uptake of the binders according to the invention by swelling is less than 150%, preferably less than 100%, of the weight of the binder. The water uptake in percent is defined by the following formula:

$$\frac{\text{Weight of hydrated binder} - \text{weight of dry binder}}{\text{Weight of dry binder}} \cdot 100\%$$

The water uptake is determined on thin films of the particular binder after allowing it to swell in water for 24 hours at room temperature and removing the water drops adhering to the surface.

The copolymers are prepared by known processes, e.g. of solution, precipitation, suspension or inverse suspension polymerization, or of emulsion or inverse emulsion polymerization, using compounds which form free radicals under polymerization conditions.

The polymerization temperatures are normally in the range from 30 to 200° C., preferably 40 to 110° C. Examples of suitable initiators are azo and peroxy compounds and the usual redox initiator systems such as combinations of hydrogen peroxide and reducing compounds, e.g. sodium sulfite, sodium bisulfite, sodium formaldehyde sulfoxylate and hydrazine.

The copolymers have K values of at least 7, preferably 10 to 100, particularly preferably 10 to 50. The K values are determined by the method of H. Fikentscher, Cellulose-Chemie, volume 13, (1932) 58–64 and 71–74, in aqueous solution or in an organic solvent at 25° C., at concentrations which are between 0.1% and 5% depending on the K value range.

Besides the polymeric binders described above, it is possible to employ up to 95% by weight, in particular up to 85% by weight and preferably up to 75% by weight of other binders, based on the total weight of binder. If present, in general at least 0.1% by weight, preferably at least 0.5% by weight, of the other binder is employed. Those suitable are polymers, copolymers, cellulose derivatives, starch and starch derivatives, for example:

Polyvinylpyrrolidone (PVP), copolymers of N-vinylpyrrolidone (NVP) and vinyl acetate or vinyl propionate, copolymers of vinyl acetate and crotonic acid, partially hydrolyzed polyvinyl acetate, polyvinyl alcohol, poly(hydroxyalkyl acrylates), poly(hydroxyalkyl methacrylates), polyacrylates and polymethacrylates (Eudragit types), copolymers of methyl methacrylate and acrylic acid, polyacrylamides, polyethylene glycols, polyvinylformamide (where appropriate partially or completely hydrolyzed), cellulose esters, cellulose ethers, in particular methylcellulose and ethylcellulose, hydroxyalkylcelluloses, in particular hydroxypropylcellulose, hydroxyalkylalkylcelluloses, in particular hydroxypropylethylcellulose, cellulose phthalates, in particular cellulose acetate phthalate and hydroxypropylmethylcellulose phthalate, and mannans, especially galactomannans. Of these, polyvinylpyrrolidone, copolymers of N-vinylpyrrolidone and vinyl esters, poly(hydroxyalkyl acrylates), poly(hydroxyalkyl methacrylates), polyacrylates, polymethacrylates, alkylcelluloses and hydroxyalkylcelluloses are particularly preferred.

The present invention likewise relates to solid dosage forms as described above in the form of pharmaceutical dosage forms, crop treatment compositions, feed additives and dietary supplements.

The binders according to the invention are suitable for all conventional processes for producing solid dosage forms, such as granulation, grinding, compression, casting in a mold, tableting under pressure, tableting under pressure and with heat and, in particular, for extrusion or melt extrusion.

The invention further relates to a process for producing the solid dosage form described above, which comprises initially the components being, if required, melted or mixed directly, and the resulting plastic mixture being shaped to the required dosage form.

For use in melt extrusion, the polymeric binder must soften or melt in the complete mixture of all the components in the range from 50 to 180° C., preferably 60 to 130° C. The glass transition temperature of the mixture must therefore be below 180° C., preferably below 130° C. If required, it is reduced by conventional pharmacologically acceptable plasticizing additives. The amount of plasticizer does not exceed 30% of the total weight of binder and plasticizer in order to form drug forms which are stable on storage and show no cold flow. However, the mixture preferably contains no plasticizer.

Examples of such plasticizers are:

long-chain alcohols, ethylene glycol, propylene glycol, glycerol, trimethylolpropane, triethylene glycol, butanediols, pentanols such as pentaerythritol, hexanols, polyethylene glycols, polypropylene glycols, polyethylene/propylene glycols, silicones, aromatic carboxylic esters (e.g. dialkyl phthalates, trimellitic esters, benzoic esters, terephthalic esters) or aliphatic dicarboxylic esters (e.g. dialkyl adipates, sebacic esters, azelaic esters, citric and tartaric esters), fatty acid esters such as glycerol monoacetate, glycerol diacetate or glycerol triacetate or sodium diethyl sulfosuccinate. The plasticizer concentration is generally 0.5–15, preferably 0.5–5, % of the total weight of the mixture.

Usual pharmaceutical additives, the total amount of which can be up to 100% of the weight of the polymer, are, for example, extenders or bulking agents such as silicates or diatomaceous earth, magnesium oxide, aluminum oxide, titanium oxide, stearic acid or its salts, e.g. the magnesium or calcium salt, methylcellulose, sodium carboxymethylcellulose, talc, sucrose, lactose, cereal or corn starch, potato flour, polyvinyl alcohol, in particular in a concentration of 0.02–50, preferably 0.20–20, % of the total weight of the mixture;

lubricants such as aluminum and calcium stearates, talc and silicones, in a concentration of 0.1–5, preferably 0.1–3, % of the total weight of the mixture;

flow regulators such as animal or vegetable fats, in particular in hydrogenated form and those which are solid at room temperature. These fats preferably have a melting point of 50° C. or above. Triglycerides of $C_{12}$, $C_{14}$, $C_{16}$ and $C_{18}$ fatty acids are preferred. It is also possible to use waxes such as carnauba wax. These fats and waxes can advantageously be admixed alone or together with mono- and/or diglycerides or phosphatides, in particular lecithin. The mono- and diglycerides are preferably derived from the abovementioned fatty acid types. The total amount of fats, waxes, mono- and diglycerides and/or lecithins is 0.1–30, preferably 0.1–5, % of the total weight of the composition for the particular layer;

dyes such as azo dyes, organic or inorganic pigments or dyes of natural origin, with inorganic pigments in a concentration of 0.001–10, preferably 0.5–3, % of the total weight of the mixture being preferred; stabilizers such as antioxidants, light stabilizers, hydroperoxide destroyers, radical scavengers, stabilizers against microbial attack.

It is furthermore possible to add wetting agents, preservatives, disintegrants, adsorbents, mold release agents and blowing agents (cf., for example, H. Sucker et al., Pharmazeutische Technologie, Thieme-Verlag, Stuttgart 1978).

Additives for the purpose of the invention also mean substances for preparing a solid solution of the active ingredient. Examples of these additives are pentaerythritol and pentaerythritol tetraacetate, polymers such as polyethylene oxides and polypropylene oxides and their block copolymers (poloxamers), phosphatides such as lecithin, homo- and copolymers of vinylpyrrolidone, surfactants such as polyoxyethylene 40 stearate, and citric and succinic acids, bile acids, sterols and others as indicated, for example, by J. L. Ford, Pharm. Acta Helv. 61, 69–88 (1986).

Also regarded as additives are additions of bases and acids to control the solubility of an active ingredient (see, for example, K. Thoma et al., Pharm. Ind. 51, 98–101 (1989)).

The only precondition for the suitability of additives for melt extrusion is adequate thermal stability.

Active ingredients for the purpose of the invention mean all substances with a physiological effect as long as they do not decompose under the processing conditions. They are, in particular, pharmaceutical active ingredients (for humans and animals), active ingredients for crop treatment, insecticides, active ingredients for human and animal foods, fragrances and perfume oils. The amount of active ingredient per dose unit and the concentration may vary within wide limits depending on the activity and release rate. The only condition is that they suffice to achieve the desired effect. Thus, the concentration of active ingredient can be in the range from 0.1 to 95, preferably from 20 to 80, in particular 30 to 70, % by weight. It is also possible to employ combinations of active ingredients. Active ingredients for the purpose of the invention are also vitamins and minerals. The vitamins include the vitamins of the A group, the B group, meaning, besides $B_1$, $B_2$, $B_6$ and $B_{12}$ and nicotinic acid and nicotinamide, also compounds with vitamin B properties such as adenine, choline, pantothenic acid, biotin, adenylic acid, folic acid, orotic acid, pangamic acid, carnitine, p-aminobenzoic acid, myo-inositol and lipoic acid, and vitamin C, vitamins of the D group, E group, F group, H group, I and J groups, K group and P group. Active ingredients for the purpose of the invention also include therapeutic peptides. Crop treatment agents include, for example, vinclozoline, epoxiconazole and quinmerac.

The binder according to the invention is suitable, for example, for processing with the following active ingredients:

Acebutolol, acetylcysteine, acetylsalicylic acid, aciclovir, alprazolam, alfacalcidol, allantoin, allopurinol, ambroxol, amikacin, amiloride, aminoacetic acid, amiodarone, amitriptyline, amlodipine, amoxicillin, ampicillin, ascorbic acid, aspartame, astemizole, atenolol, beclomethasone, benserazide, benzalkonium-hydrochloride, benzocaine, benzoic acid, betamethasone, bezafibrate, biotin, biperiden, bisoprolol, bromazepam, bromhexine, bromocriptine, budesonide, bufexamac, buflomedil, buspirone, caffeine, camphor, captopril, carbamazepine, carbidopa, carboplatin, cefachlor, cefalexin, cefadroxil, cefazoline, cefixime, cefotaxime, ceftazidime, ceftriaxone, cefuroxime, selegiline, chloramphenicol, chlorhexidine, chlorpheniramine, chlortalidone, choline, cyclosporin, cilastatin, cimetidine, ciprofloxacin, cisapride, cisplatin, clarithromycin, clavulanic acid, clomipramine, clonazepam, clonidine, clotrimazole, codeine, cholestyramine, cromoglycinic acid, cyanocobalamin, cyproterone, desogestrel, dexamethasone, dexpanthenol, dextromethorphan, dextropropoxiphene, diazepam, diclofenac, digoxin, dihydrocodeine, dihydroergotamine, dihydroergotoxin, diltiazem, diphenhydramine, dipyridamole, dipyrone, disopyramide, domperidone, dopamine, doxycycline, enalapril, ephedrine, epinephrine, ergocalciferol, ergotamine, erythromycin, estradiol, ethinylestradiol, etoposide, Eucalyptus globulus, famotidine, felodipine, fenofibrate, fenoterol, fentanyl, flavine mononucleotide, fluconazole, flunarizine, fluorouracil, fluoxetine, flurbiprofen, furosemide, gallopamil, gemfibrozil, gentamicin, Gingko biloba, glibenclamide, glipizide, clozapine, Glycyrrhiza glabra, griseofulvin, guaifenesin, haloperidol, heparin, hyaluronic acid, hydrochlorothiazide, hydrocodone, hydrocortisone, hydromorphone, ipratropium hydroxide, ibuprofen, imipenem, indomethacin, iohexol, iopamidol, isosorbide dinitrate, isosorbide mononitrate, isotretinoin, itraconazole, ketotifen, ketoconazole, ketoprofen, ketorolac, labetalol, lactulose, lecithin, levocarnitine, levodopa, levoglutamide, levonorgestrel, levothyroxine, lidocaine, lipase, imipramine, lisinopril, loperamide, lorazepam, lovastatin, medroxyprogesterone, menthol, methotrexate, methyldopa, methylprednisolone, metoclopramide, metoprolol, miconazole, midazolam, minocycline, minoxidil, misoprostol, morphine, multivitamin mixtures and combinations and mineral salts, N-methylephedrine, naftidrofuryl, naproxen, neomycin, nicardipine, nicergoline, nicotinamide, nicotine, nicotinic acid, nifedipine, nimodipine, nitrazepam, nitrendipine, nizatidine, norethisterone, norfloxacin, norgestrel, nortriptyline, nystatin, ofloxacin, omeprazole, ondansetron, pancreatin, panthenol, pantothenic acid, paracetamol, penicillin G, penicillin V, phenobarbital, pentoxifylline, phenoxymethylpenicillin, phenylephrine, phenylpropanolamine, phenytoin, piroxicam, polymyxin B, povidone-iodine, pravastatin, prazepam, prazosin, prednisolone, prednisone, bromocriptine, propafenone, propranolol, proxyphylline, pseudoephedrine, pyridoxine, quinidine, ramipril, ranitidine, reserpine, retinol, riboflavin, rifampicin, rutoside, saccharin, salbutamol, salcatonin, salicylic acid, simvastatin, somatropin, sotalol, spironolactone, sucralfate, sulbactam, sulfamethoxazole, sulfasalazine, sulpiride, tamoxifen, tegafur, teprenone, terazosin, terbutaline, terfenadine, tetracycline, theophylline, thiamine, ticlopidine, timolol, tranexamic acid, tretinoin, triamcinolone acetonide, triamterene, trimethoprim, troxerutin, uracil, valproic acid, vancomycin, verapamil, vitamin E, folinic acid, zidovudine.

Preferred active ingredients are ibuprofen (as racemate, enantiomer or enriched enantiomer), ketoprofen, flurbiprofen, acetylsalicylic acid, verapamil, paracetamol, nifedipine or captopril.

The solid dosage forms are produced by preparing a plastic mixture of the components (melt) and subjecting it to a shaping step. The mixing of the components and the formation of the melt can take place in a variety of ways. The mixing can take place before, during and/or after the formation of the melt. For example, the components can be mixed first and then melted or be mixed and melted simultaneously. The plastic mixture is frequently also homogenized in order to disperse the active ingredient efficiently.

However, it has proven preferable, especially on use of sensitive active ingredients, first to melt and premix the polymeric binder, where appropriate together with conventional pharmaceutical additives, and then to mix in (homogenize) the sensitive active ingredient(s) in plastic phase with very short residence times in "intensive mixers". The active ingredient(s) can in this case be employed in solid form or as solution or dispersion.

The components are generally employed as such in the production process. However, they can also be used in liquid form, i.e. as solution, suspension or dispersion.

A solvent which is primarily suitable for the liquid form of the components is water or a water-miscible organic solvent or a mixture thereof with water. However, solvents which can be used are also organic solvents which are immiscible or miscible with water. Suitable water-miscible solvents are, in particular, $C_1$–$C_4$-alkanols such as ethanol, isopropanol or n-propanol, polyols such as ethylene glycol, glycerol and polyethylene glycols. Suitable water-immiscible solvents are alkanes such as pentane or hexane, esters such as ethyl acetate or butyl acetate, chlorinated hydrocarbons such as methylene chloride, and aromatic hydrocarbons such as toluene and xylene. Another solvent which can be used is liquid $CO_2$.

The solvent used in the particular case depends on the component to be taken up and its properties. For example, pharmaceutical active ingredients are frequently used in the form of a salt which is generally soluble in water. Water-soluble active ingredients can therefore be employed as aqueous solution or, preferably, be taken up in the aqueous solution or dispersion of the binder. A corresponding statement applies to active ingredients which are soluble in one of the solvents mentioned, when the liquid form of the component used is based on an organic solvent.

It is possible where appropriate to replace the melting by dissolving, suspending or dispersing in the abovementioned solvents, if required and/or necessary with the addition of suitable additives such as emulsifiers. The solvent is then generally removed to form the melt in a suitable apparatus, e.g. an extruder. This will be comprised by the term mixing hereinafter.

The melting and/or mixing takes place in an apparatus customary for this purpose. Particularly suitable ones are extruders or containers which can be heated where appropriate and have an agitator, e.g. kneaders (like those of the type to be mentioned below).

A particularly suitable mixing apparatus is one employed for mixing in plastics technology. Suitable apparatuses are described, for example, in "Mischen beim Herstellen und Verarbeiten von Kunststoffen", H. Pahl, VDI-Verlag, 1986. Particularly suitable mixing apparatuses are extruders and dynamic and static mixers, and stirred vessels, single-shaft stirrers with stripper mechanisms, especially paste mixers, multishaft stirrers, especially PDSM mixers, solids mixers and, preferably, mixer/kneader reactors (e.g. ORP, CRP, AP, DTB supplied by List or Reactotherm supplied by Krauss-Maffei or Ko-kneader supplied by Buss), trough mixers or internal mixers or rotor/stator systems (e.g. Dispax supplied by IKA).

In the case of sensitive active ingredients it is preferable first for the polymeric binder to be melted in an extruder and then for the active ingredient to be admixed in a mixer/kneader reactor. On the other hand, with less sensitive active ingredients, a rotor/stator system can be employed for vigorously dispersing the active ingredient.

The mixing apparatus is charged continuously or batchwise, depending on its design, in a conventional way. Powdered components can be introduced in a free feed, e.g. via a weigh feeder. Plastic compositions can be fed in directly from an extruder or via a gear pump, which is particularly advantageous if the viscosities and pressures are high. Liquid media can be metered in by a suitable pump unit.

The mixture obtained by mixing and/or melting the binder, the active ingredient and, where appropriate, the additive(s) ranges from pasty to viscous (plastic) or fluid and is therefore extrudable. The glass transition temperature of the mixture is below the decomposition temperature of all the components present in the mixture. The binder should preferably be soluble or swellable in a physiological medium.

The steps of mixing and melting in the process can be carried out in the same apparatus or in two or more separately operating apparatuses. The preparation of a premix can take place in one of the conventional mixing apparatuses described above. A premix of this type can then be fed in directly, for example into an extruder, and subsequently extruded, where appropriate with the addition of other components.

It is possible in the process according to the invention to employ as extruders single screw machines, intermeshing screw machines or else multiscrew extruders, especially twin screw extruders, corotating or counterrotating and, where appropriate, equipped with kneading disks. If it is necessary in the extrusion to evaporate a solvent, the extruders are generally equipped with an evaporating section. Particularly preferred extruders are those of the ZKS series from Werner & Pfleiderer.

It is also possible according to the invention to produce multilayer pharmaceutical forms by coextrusion, in which case a plurality of mixtures of the components described above are fed together to an extrusion die so as to result in the required layered structure of the multilayer pharmaceutical form. It is preferable to use different binders for different layers.

Multilayer drug forms preferably comprise two or three layers. They may be in open or closed form, in particular as open or closed multilayer tablets.

At least one of the layers contains at least one pharmaceutical active ingredient. It is also possible for another active ingredient to be present in another layer. This has the advantage that two mutually incompatible active ingredients can be processed or that the release characteristics of the active ingredient can be controlled.

The shaping takes place by coextrusion with the mixtures from the individual extruders or other units being fed into a common coextrusion die and extruded. The shape of the coextrusion die depends on the required pharmaceutical form. Examples of suitable dies are those with a flat orifice, called a slit die, and dies with an annular orifice. The design of the die depends on the polymeric binder used and the required pharmaceutical form.

The resulting mixture is preferably solvent-free, i.e. it contains neither water nor an organic solvent.

The plastic mixture is, as a rule, subjected to final shaping. This can result in a large number of shapes depending on the die and mode of shaping. For example, if an extruder is used, the extrudate can be shaped between a belt and a roll, between two belts or between two rolls, as described in EP-A 358 105, or by calendering in a calender with two molding rolls, see, for example, EP-A 240 904. Other shapes can be obtained by extrusion and hot- or cold-cut of the extrudate, for example small-particle and uniformly shaped pellets. Hot-cut pelletization usually results in lenticular dosage forms (tablets) with a diameter of 1–10 mm, while strip pelletization normally results in cylindrical products with a length to diameter ratio of from 1 to 10 and a diameter of from 0.5 to 10 mm. It is thus possible to produce monolayer but also, on use of coextrusion, open or closed multilayer dosage forms, for example oblong tablets, coated tablets, pastilles and pellets. The resulting granules can then also be ground to a powder and compressed to tablets in a conventional way. Micropastilles can be produced by the Rotoform-Sandvik process. These dosage forms can be rounded and/or provided with a coating by conventional methods in a subsequent process step. Examples of materials suitable for film coatings are polyacrylates such as the Eudragit types, cellulose esters, such as the hydroxypropylcellulose phthalates, and cellulose ethers such as ethylcellulose, hydroxypropylmethylcellulose or hydroxypropylcellulose.

In specific cases there may be formation of solid solutions. The term solid solutions is familiar to the skilled worker, for example from the literature cited at the outset. In solid solutions of active ingredients in polymers, the active ingredient is in the form of a molecular dispersion in the polymer.

The following examples are intended to illustrate the process according to the invention without, however, restricting it. The calendering of the extruded melt took place as described in EP-A 240 904.

EXAMPLES

The extrusion took place in each case using a Werner and Pfleiderer ZKS 30 twin screw extruder with 5 sections under the conditions stated in each example.

Example 1

520 g of copolymer of 50% by weight of vinylpyrrolidone, 20% by weight of methyl methacrylate and 30% by weight of vinyl acetate (K value 31.4; 1% strength in acetone) were extruded with 480 g of verapamil hydrochloride and calendered to give 500 mg oblong tablets.

The extrusion took place under the following conditions:

| | |
|---|---|
| Section 1 | 53° C. |
| Section 2 | 89° C. |
| Section 3 | 134° C. |
| Section 4 | 117° C. |
| Section 5 | 109° C. |
| Die | 100° C. |

The release of the active ingredient from the tablets was investigated by the USP paddle method (pH change). It was 22% after 1 hour, 31% after 2 hours and 57% after 8 hours.

Example 2

520 g of copolymer of 50% by weight of vinylpyrrolidone, 30% by weight of methyl methacrylate and 20% by weight of vinyl acetate (K value 32.4; 1% strength in acetone) were extruded with 480 g of verapamil hydrochloride and calendered.

The extrusion took place under the following conditions:

| | |
|---|---|
| Section 1 | 49° C. |
| Section 2 | 88° C. |
| Section 3 | 133° C. |
| Section 4 | 116° C. |
| Section 5 | 107° C. |
| Die | 101° C. |

The release of the active ingredient from the tablets was investigated by the USP paddle method (pH change). It was 25% after 1 hour, 39% after 2 hours and 73% after 8 hours.

Example 3

252 g of copolymer of 50% by weight of vinylpyrrolidone, 20% by weight of methyl methacrylate and 30% by weight of vinyl acetate (K value 31.4; 1% strength in acetone) were extruded with 60 g of Kollidon 30 (polyvinylpyrrolidone) and 288 g of verapamil hydrochloride and calendered to give 500 mg oblong tablets.

The extrusion took place under the following conditions:

| | |
|---|---|
| Section 1 | 23° C. |
| Section 2 | 60° C. |
| Section 3 | 93° C. |
| Section 4 | 133° C. |
| Section 5 | 114° C. |
| Die | 93° C. |

The release of the active ingredient from the tablets was investigated by the USP paddle method (pH change). It was 25% after 1 hour, 37% after 2 hours and 63% after 8 hours.

Example 4

252 g of copolymer of 50% by weight of vinylpyrrolidone, 25% by weight of methyl methacrylate and 25% by weight of vinyl acetate (K value 31.5; 1% strength in acetone) were extruded with 60 g of Kollidon VA 64 (polyvinylpyrrolidone) and 288 g of verapamil hydrochloride and calendered to give 500 mg oblong tablets.

The extrusion took place under the following conditions:

| | |
|---|---|
| Section 1 | 23° C. |
| Section 2 | 42° C. |
| Section 3 | 83° C. |
| Section 4 | 131° C. |
| Section 5 | 100° C. |
| Die | 95° C. |

The release of the active ingredient from the tablets was investigated by the USP paddle method (pH change). It was 7% after 1 hour, 41% after 2 hours and 74% after 8 hours.

Example 5

282 g of copolymer of 50% by weight of vinylpyrrolidone, 30% by weight of methyl methacrylate and 20% by weight of vinyl acetate (K value 32.4; 1% strength in acetone) were extruded with 30 g of Klucel EF (hydroxypropylcellulose) and 288 g of verapamil hydrochloride and calendered to give 500 mg oblong tablets.

The extrusion took place under the following conditions:

| | |
|---|---|
| Section 1 | 23° C. |
| Section 2 | 47° C. |
| Section 3 | 90° C. |
| Section 4 | 131° C. |
| Section 5 | 113° C. |
| Die | 96° C. |

The release of the active ingredient from the tablets was investigated by the USP paddle method (pH change). It was 26% after 1 hour, 38% after 2 hours and 65% after 8 hours.

Example 6

252 g of copolymer of 50% by weight of vinylpyrrolidone, 30% by weight of methyl methacrylate and 20% by weight of vinyl acetate (K value 32.4; 1% strength in acetone) were extruded with 60 g of Klucel EF (hydroxypropylcellulose) and 288 g of verapamil hydrochloride and calendered to give 500 mg oblong tablets.

The extrusion took place under the following conditions:

| | |
|---|---|
| Section 1 | 23° C. |
| Section 2 | 55° C. |
| Section 3 | 94° C. |
| Section 4 | 132° C. |
| Section 5 | 114° C. |
| Die | 95° C. |

The release of the active ingredient from the tablets was investigated by the USP paddle method (pH change). It was 43% after 1 hour, 67% after 2 hours and 92% after 8 hours.

Example 7

160 g of copolymer of 50% by weight of vinylpyrrolidone, 30% by weight of methyl methacrylate and 20% by weight of vinyl acetate (K value 51.5; 1% strength in acetone) were directly tableted with 3.4 mg of Aerosil 200, 1.6 mg of magnesium stearate and 160 mg of propranolol hydrochloride under a force of 18 kN to give a bevelled 10 mm tablet.

The release of the active ingredient from the tablets was investigated by the USP paddle method (pH 7.4). It was 16% after 1 hour, 25% after 2 hours, 61% after 8 hours and 95% after 16 hours.

Example 8

160 mg of copolymer of 40% by weight of vinylpyrrolidone, 40% by weight of methyl methacrylate and 20% by weight of vinyl acetate (K value 40.1; 1% strength in acetone) were directly tableted with 3.4 mg of Aerosil 200, 1.6 mg of magnesium stearate and 160 mg of propranolol hydrochloride under a force of 18 kN to give a bevelled 10 mm tablet.

The release of the active ingredient from the tablets was investigated by the USP paddle method (pH 7.4). It was 41% after 1 hour, 50% after 2 hours, 71% after 8 hours and 95% after 16 hours.

Comparative Example 1

500 g of copolymer of 60% by weight of N-vinylpyrrolidone and 40% by weight of vinyl acetate are extruded with 500 g of verapamil hydrochloride under the conditions indicated below and calendered to give 500 mg oblong tablets.

The extrusion took place under the following conditions:

| | |
|---|---|
| Section 1 | 90° C. |
| Section 2 | 100° C. |
| Section 3 | 110° C. |
| Section 4 | 120° C. |
| Section 5 | 130° C. |
| Die | 135° C. |

The release of the active ingredient from the tablets was investigated by the USP paddle method (pH change). It was 100% after 3 hours.

Comparative Example 2

500 g of copolymer of 30% by weight of vinylpyrrolidone and 70% by weight of vinyl acetate are extruded with 500 g of verapamil hydrochloride under the conditions indicated below and calendered to give 500 mg oblong tablets.

The extrusion took place under the following conditions:

| | |
|---|---|
| Section 1 | 30° C. |
| Section 2 | 60° C. |
| Section 3 | 100° C. |
| Section 4 | 100° C. |
| Section 5 | 120° C. |
| Die | 120° C. |

The release of the active ingredient from the tablets was investigated by the USP paddle method (pH change). It was 100% after 8 hours.

We claim:

1. A solid dosage form comprising at least one polymeric binder, and at least one active ingredient wherein the polymeric binder consists essentially of copolymerization units of a) 30–65% by weight of at least one N-vinyllactam of the formula I

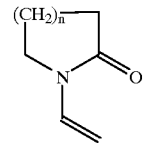

(I)

in which n is 1,2, or 3, b) 20–55% by weight of methyl methacrylate, c) 15–50% by weight of at least one other monomer selected from vinyl esters of aliphatic $C_1$–$C_{22}$-carboxylic acids, esters of α, β-ethylenically unsaturated $C_3$–$C_8$-mono- and dicarboxylic acids wight $C_1$–$C_8$-alkanols, $C_1$–$C_4$-diols or di-($C_1$–$C_4$-alkyamino-$C_1$–$C_4$-alkanols, amides, nitriles, and cyclic anhydrides of the carboxylic acids, and d) 0–5% by weight of at least on α, β-ethylenically unsaturated acid selected from $C_3$–$C_8$-mono- and -dicarboxylic acids, noncyclic anhydrides of these carboxylic acids, monoesters of the $C_3$–$C_8$-dicarboxylic acids, α, β-ethylenically unsaturated sulfonic acids and the salts or quaternized products thereof.

2. A solid dosage form as claimed in claim 1, wherein the N-vinyllactam is N-vinylpyrrolidone.

3. A solid dosage form as claimed in claim 1, wherein the other monomers c) are vinyl esters of aliphatic $C_1$–$C_{22}$-carboxylic acids.

4. A pharmaceutical composition, crop treatment composition, feed additive or dietary supplement comprising the dosage form of claim 1.

* * * * *

UNITED STATES PATENT AND TRADEMARK OFFICE
CERTIFICATE OF CORRECTION

PATENT NO. : 6,284,803 B1 Page 1 of 1
DATED : September 4, 2001
INVENTOR(S) : Kothrade et al.

It is certified that error appears in the above-identified patent and that said Letters Patent is hereby corrected as shown below:

<u>Column 14, claim 1,</u>
Line 28, "wight" should be -- with --.

Signed and Sealed this

Fifth Day of March, 2002

Attest:

JAMES E. ROGAN
*Attesting Officer*     *Director of the United States Patent and Trademark Office*